United States Patent [19]

Nussbaum

[11] Patent Number: 4,692,279

[45] Date of Patent: Sep. 8, 1987

[54] PREPARATION OF ACYLOXY BENZENE SULFONATE

[75] Inventor: Marvin Nussbaum, Skokie, Ill.

[73] Assignee: Stepan Company, Northfield, Ill.

[21] Appl. No.: 723,217

[22] Filed: Apr. 15, 1985

[51] Int. Cl.[4] .................... C07C 143/90; C07C 69/00
[52] U.S. Cl. ............................ 260/402; 260/505 E; 260/505 S; 260/505 N; 560/142; 252/552
[58] Field of Search .............. 260/402, 505 E, 505 S, 260/505 N; 560/142; 252/552

[56] References Cited

U.S. PATENT DOCUMENTS

| | | | |
|---|---|---|---|
| 3,169,142 | 2/1965 | Knaggs et al. | 260/505 E |
| 3,358,017 | 12/1967 | Seifert | 260/505 N |
| 4,148,821 | 4/1979 | Nussbaum et al. | 260/505 S |
| 4,390,474 | 6/1983 | Nussbaum et al. | 260/505 S |
| 4,588,533 | 5/1986 | Berry | 260/402 |

FOREIGN PATENT DOCUMENTS 545620  9/1957  Canada ..................... 260/505 E

*Primary Examiner*—Paul J. Killos

[57] ABSTRACT

A process is provided for making acyloxy benzene sulfonates by the steps of sulfonating with $SO_3$, digesting the sulfonation adduct, and neutralizing. The sulfonation adduct can spontaneously rearrange. Unless the rearrangement is controlled as taught in the sulfonating and digesting steps, product yields of acyloxy benzene sulfonate drop to unusable levels and the color of the product is poor and the content of by-products is excessive in the product.

13 Claims, No Drawings

PREPARATION OF ACYLOXY BENZENE SULFONATE

BACKGROUND OF THE INVENTION

1. Field of the Invention

This invention lies in the field of sulfonating acyloxy benzene esters with sulfur trioxide.

2. Prior Art

Knaggs and Nussbaum U.S. Pat. No. 3,169,142 taught a continuous process for sulfation and sulfonation of liquid organic compounds with sulfur trioxide, by contacting a liquid film of an organic compound with a gaseous mixture of sulfur trioxide and inert gas. The resulting product was commonly then neutralized with aqueous base, particularly when making sulfonates having utility as surfactants.

It was appreciated in practicing this process that a small (up to 1.5 weight percent) increase in desired sulfonic acid yield could be obtained in the sulfonation of an alkyl benzene to produce directly the corresponding intermediate sulfonic acid, such as, for example, dodecylbenzene sulfonic acid, by allowing a short holding period to occur between sulfonation and neutralization. This holding period produced such a yield increase because of the reaction of residual quantities of $SO_3$, present with unreacted alkyl benzene starting feed. No rearrangement is involved.

Esters, such as methyl esters and fatty acid glycerides, are mentioned among many other compounds, in Knaggs and Nussbaum '142 as feedstocks for sulfonation (see col. 3, lines 24-30). In ester sulfonation, the $SO_3$ apparently preliminarily forms an adduct with the carboxyl group. This adduct can be and preferably is rearrangeable to produce sulfonic acid intermediate products before neutralization. In the case of fatty acid methyl esters, the rearrangement is characteristically endothermic, and alpha sulfonated products result. So far as is now known, no class of esters was previously known whose $SO_3$ adduct would or could rearrange to produce a ring substituted sulfonic acid.

The practice of the Knaggs and Nussbaum '142 process with ester and other previously employed organic feedstocks characteristically produces side reactions in addition to a main or primary reaction. Thus, it is not easy, and sometimes not even possible, to produce directly by this process high yields of relatively pure sulfated or sulfonated product species, such as is desired and even necessary for many individual and commercial purposes. Terminal purification procedures are sometimes necessary in order to obtain sulfonated products of a desired purity. Such purification procedures are undesired since they add to the cost of making a product.

Recently, it has been proposed to use acyloxy benzene sulfonate compounds, of the class wherein the acyl group is derived from a fatty acid, in commercial detergent formulations. Large-scale usage appears to require a synthetic route for making such compounds which is inexpensive and capable of producing a relatively high purity product in high yield.

The indicated Knaggs and Nussbaum process would at first appear to offer promise as a potentially inexpensive synthetic route for making these compounds by sulfonating the corresponding phenyl ester. So far as is now known, no one has previously prepared acyloxy benzene sulfonate by direct synthesis with $SO_3$ from acyloxy benzene. However, when one attempts to practice such '142 patent teachings of Knaggs and Nussbaum to sulfonate an acyloxy benzene, various formidable unexpected problems arise, some of which appear never heretofore to have been experienced in $SO_3$ sulfonation of organic compounds, especially esters. These problems result in yields of acyloxy benzene sulfonates that are so low as not to be of apparent commercial practicality or feasibility. Further, the desired product is accompanied by significant quantities of unwanted by-products, for example, sulfones and phenolic materials, which detract even further from the commercial value or practicality of using such so-produced acyloxy benzene sulfonates in surfactant formulations.

One of the yield-reducing problems which can arise when sulfonating is the occurrence of degradation which is undesired and which results from the reactivity of the sulfur trioxide with acyloxy benzene. Degradation not only reduces the yield of the desired acyloxy benzene sulfonate, but also produces by-products which adversely affect desired product characteristics, such as color and shelf-life stability.

Moreover, if one attempts to follow prior art teachings as regards use of a heated digestion zone between sulfonation and neutralization, then both side reactions and degradation problems are compounded and yields of acyloxy benzene sulfonate go down. Thus, the sulfonation process taught by the Knaggs and Nussbaum 142 patent is not suitable for directly making acyloxy benzene sulfonates of commercially acceptable quality and purity. At the least, it appears that with this process some sort of a special terminal "clean-up" step would be needed to produce a light color product with a content of acyloxy benzene sulfonate above about 70 weight percent (total product solids weight basis). However, such "clean-up" step would only undesirably add to the cost of making the final product.

Apart from the foregoing considerations with regard to sulfonation, the prior art has heretofore appreciated that the conditions employed in neutralization of an organosulfonic acid ester can affect yields of the resulting desired product salt. For example, unless the temperature and the pH at which neutralization is accomplished with a material such a sulfonic acid of an aliphatic carboxylic acid ester are controlled, such as, for example, an alpha sulfo methyl fatty acid ester, one can wind up with a neutralized product which is substantially hydrolyzed. In the case of neutralizing acyloxy benzene sulfonate acid, control of neutralization using special conditions is necessary in order to avoid hydrolysis of this acid.

Thus, the prior art does not provide any sulfonation process which permits one to produce acyloxy benzene sulfonates in high yield and in high purity.

BRIEF SUMMARY OF THE INVENTION

There has now been unexpectedly discovered a new and very useful process for making acyloxy benzene sulfonates of high purity and in high yields utilizing a direct sulfonation of acyloxy benzene with sulfur trioxide ($SO_3$), a controlled digestion procedure, and then a following special neutralization procedure for the intermediately produced acyloxy benzene sulfonic acid to produce a salt thereof.

The use of a temperature controlled digestion step appears to be novel in the sulfonation art.

The sulfonation step results in the production of a new and unusual class of adducts of $SO_3$ with acyloxy benzene. These adducts can be used, in accordance with the process of this invention, to product acyloxy benzene sulfonic acid as taught herein.

This process results in the direct production (without any intervening purification step) of a new and very useful class of compositions which comprise mainly neutralized acyloxy benzene sulfonate salt in combination with minor amounts of certain organic impurities. These compositions can be produced as aqueous solutions or in the form of dried solids. These compositions are characterized by being substantially colorless and by having excellent storage characteristics. Thus, the impurities do not interfere with characteristics of the acyloxybenzene sulfonate or with the ability to use such in surfactant and detergent formulations.

This process overcomes the above-described difficulties experienced, for example, when one attempts to utilize the Knaggs and Nussbaum process of U.S. Pat. No. 3,169,142 for sulfonating acyloxy benzene to produce acyloxy benzene sulfonates in high yield and with high purity.

In the present sulfonation procedure, substantially pure acyloxy benzene is contacted with $SO_3$ under special conditions which (a) moderate the ensuing addition reaction, (b) maximize production of preferably a 1:1 molar adduct of $SO_3$ with acyloxy benzene, and (c) minimize production of unwanted by-products, (d) minimize formation of colored impurities, and (e) control any rearrangement during sulfonation of the adduct-containing reaction product.

Surprisingly and unexpectedly, an $SO_3$ acyloxy benzene adduct intermediate formed by $SO_3$ contacting, even when produced in an impure form, such as might be produced generally by following prior art sulfonation teachings, displays a remarkable tendency to rearrange with great exothermiscity. The rearrangement can result in a ring substituted sulfonic acid. Such an exothermic rearrangement of an $SO_3$ adduct has never previously been reported, so far as is now known. For example, if an $SO_3$-acyloxy benzene adduct is formed at room temperature, then within about 30 seconds of its formation, the reaction mass will have risen to a temperature which is characteristically over about 100° C. The uncontrolled combination after adduct formation of rapid rearrangement with associated evolution of substantial heat results in a rearranged product of poor color which contains excessive amounts of unwanted by-products along with the corresponding acyloxy benzene sulfonic acid derivative.

In accordance with one primary aspect of the present invention, a process is provided for controlling the formation of an $SO_3$ acyloxy benzene adduct and for controlling the rearrangement of such adduct in a digestion procedure so that yields of an acyloxy benzene sulfonic acid derivative preferably in excess of about 80 weight percent, and more preferably above about 87%, are routinely obtainable from the intermediate $SO_3$-acyloxy benzene adduct. To achieve such controls, the present invention provides a set of sulfonation and digestion conditions which are conducted at controlled temperatures which are novel in the ester sulfonation art. Further, to achieve such controls, the sulfonation step is practiced under special conditions which minimize color formation, by-product formation and adduct degradation during the sulfonation process.

The high purity acyloxy benzene sulfonic acid derivative, once formed by the practice of the process steps of the present invention, is relatively stable even at ambient conditions. In commercial practice, however, the sulfonic acid intermediate is converted (neutralized) under aqueous liquid phase conditions into a salt, especially a salt of a cation selected from the group consisting of alkali metals, alkaline earth metals, and ammonium. Sodium is presently a most preferred cation.

Thus, after digestion, the resulting acyloxy benzene sulfonic acid is preferably neutralized. To minimize ester hydrolysis and to avoid loss in yield of the desired acyloxybenzene sulfonate salt product, neutralization is preferably carried out by contacting the acyloxy benzene sulfonic acid with an inorganic hydroxide whose cation is selected from the group consisting of alkali metals, alkaline earth metals, ammonium, and mixtures thereof (preferably sodium) under aqueous liquid phase conditions. Preferably, the inorganic hydroxide is preliminarily dissolved in water to provide an aqueous solution. For example, such a solution can contain from about 5 to 50 weight percent of dissolved inorganic hydroxide.

The resulting neutralized acyloxy benzene sulfonate salt then either is used as such in solution form, or is dried to produce a powder (the latter being presently preferred). Drying can be carried out by any convenient procedure, but spray drying is presently preferred. The acyloxy benzene sulfonate salt product is typically directly formulatable without any clean-up or purification step with other components, as desired, to produce synthetic detergent compositions, surfactant blends, and the like.

Various objects, aims, purposes, features, advantages, variations, alterations, modifications, and the like, will become apparent to those skilled in the art from the teachings of the present specification taken with the appended claims.

DETAILED DESCRIPTION

Acyloxy Benzene

An acyloxy benzene starting material employed in the practice of the process of the present invention is preferably substantially pure, that is, a starting acyloxy benzene is at least about 98 weight percent pure. Typically and preferably the impurities when and if present in combination therewith comprise phenol, fatty acid, ketone phenol, or the like. Most preferably, a starting acyloxy benzene is at least about 99 weight percent pure.

Various synthetic methods are available in the prior art for producing acyloxy benzene; see, for example, JAOCS 32, p. 170.

In general, such a starting material employed in the practice of the present invention comprises at least one acyloxy benzene of the following formula:

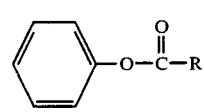
(1)

where R is a saturated aliphatic group containing from about 2 to 19 carbon atoms inclusive.

Presently preferred acyloxy benzene compounds of formula (1) above are characterized by those wherein R is a saturated aliphatic group containing 7, 8, or 9 carbon atoms each, that is, phenyl octanoate, phenyl nonanoate, phenyl isononanoate, and/or phenyl decanoate. Straight or branched chain alkyl radicals can preferably be used.

Sulfonation

In general, sulfonation of acyloxy benzene with $SO_3$ in accordance with the teachings of the present invention is conducted by contacting liquid or gaseous (or mixture thereof) $SO_3$ with at least one acyloxy benzene starting material (as described above) which is in a liquid phase. The contacting is carried out at an average temperature below about 50° C. and preferably below about 30° C.

In order to obtain the high-purity yields of a product acyloxy benzene sulfonate salt as desired by the practice of the present invention, it is necessary to control the temperature of the sulfonation reaction mass so as to make this temperature as low as practical. In general, such average temperature should be lower than about 50° C. and preferably below about 30° C. Thus, it is presently preferred to utilize an average contacting temperature for $SO_3$ and acyloxybenzene which ranges from about $-30°$ to $+50°$ C. and more preferably from about $-10°$ to $+30°$ C. Such temperatures (a) maximize the yield of the desired $SO_3$-acyloxy benzene adduct, and (b) minimize the occurrence of (1) color formation, (2) by-product formation, and (3) adduct degradation during residency of a reaction mass in a sulfonation reaction zone.

In the sulfonation reaction zone, the initial mole ratio of $SO_3$ to acyloxy benzene can range from about 0.9 to 1.1, and preferably from about 0.95 to 1.05.

Also, in the sulfonation zone, a diluent (gaseous, or preferably liquid, or mixture thereof) can be present. The presence of a diluent is presently preferred, because such permits an improved capacity to regulate the temperature in the sulfonation reaction zone. The adduct forming reaction is itself apparently exothermic, and it is desirable to avoid heat build-up on a localized basis during sulfonation.

Heat exchange capacity located in functional association with the sulfonation reaction zone is desirable in order to remove heat of reaction, and use of such is preferred in practicing this invention for temperature control and maintenance in this raction zone.

Various combinations of contacting conditions can be employed for any given sulfonation as shown by the following examples of sulfonation techniques:

(A) Falling Film.

One may employ the falling film sulfonation apparatus described in Knaggs and Nussbaum U.S. Pat. No. 3,169,142. Here, a falling liquid film is mainly comprised of acyloxy benzene, while a gas phase is provided by a gaseous composition comprised of a mixture of sulfur trioxide and substantially inert gas wherein a proportion within the range of from about 5:1 to 50:1 of inert gas to sulfur trioxide by volume is employed. The inert gas can be as described in the Knaggs and Nussbaum '142 patent (see column 3, lines 45 through 52 thereof), or otherwise, if desired. The confining reaction zone formed by the heat exchange surface upon which the falling film is supported and confined is preferably exteriorly jacketed so that a heat exchange fluid can be circulated in heat exchange relationship thereto so that the average temperature of the reaction zone is maintained below about 50° C. and preferably below about 30° C. Similarly, and preferably, the temperatures of the liquid feed and of the gaseous feed are likewise regulatable and also the temperature of the liquid effluent can be monitored.

(B) Batch.

The acyloxy benzene is preliminarily dissolved in a solvent such as a low boiling liquid diluent which preferably boils below about 10° C. although higher boiling such diluents can be used. One presently preferred such diluent comprises liquid sulfur dioxide. Preferably a reactant such as sulfur trioxide is then admixed with (dissolved in) the resulting solution and a contacting as desired is achieved between the starting acyloxy benzene and the sulfur trioxide. Acyloxy benzene is soluble in $SO_2$ and in other lower boiling liquid diluents. Mixing of reactants in such a liquid diluent is preferred during such contacting to avoid localized oversulfonation. Because $SO_2$ boils at atmospheric pressure at about $-10°$ C., it is necessary to maintain the reaction or contacting zone under pressurized conditions during sulfonation when $SO_2$ is used as a liquid diluent. For reasons of practicality, as well as for reasons of maximizing production of the desired adduct, it is presently here most preferred to maintain the reaction zone at a temperature below about 15° C. Liquid phase conditions can be maintained at such temperatures by employing pressures in the range of from about 5 to 20 pounds per square inch gauge.

Although sulfur dioxide in liquid form is a preferred diluent or solvent for use in liquid phase sulfonation of acyloxy benzene, other low boiling liquid diluents or solvents may be employed, such as a perfluorinated hydrocarbon (e.g., a member of the "Freon" family), ethylene dichloride, methylene chloride, carbon tetrachloride, heptane, and the like. Such a solvent, when used for liquid phase sulfonation, should preferably boil below the indicated preferred upper digestion temperature employed in the practice of the present invention. In general, it is preferred to remove such a solvent before the subsequent digestion step is completed by boiling, venting, or the like.

Batch sulfonation techniques suitable for use in the practice of this invention include:

(1) Acyloxy benzene dissolved in a solvent and addition of liquid $SO_3$ thereto.

(2) Acyloxy benzene dissolved in a solvent and addition of gaseous $SO_3$ thereto.

(3) Each of acyloxy benzene and $SO_3$ separately dissolved in a solvent and the resulting solutions admixed together; and the like.

In summary, the general conditions employed for sulfonation are shown in the following Table I:

TABLE I

| | SULFONATION CONDITIONS | |
| --- | --- | --- |
| | Value Range | |
| Condition | Preferred | More Preferred |
| Contacting Temperature | about $-20$ to 50° C. | about $-10$ to $+30°$ C. |
| Combined Mole Ratio of $SO_3$ to Acyloxy Benzene | about 0.9 to 1.1 | about 1 |
| Ratio of Solvent: Ester wt:wt | about 0.1 to 3.0 | about 0.5 to 1.0 |

During sulfonation, the mole ratio of $SO_3$ to acyloxy benzene can vary, but preferably is maintained within the ranges of indicated, the localized instantaneous mole ratio being dependant upon the particular technique being employed and other related factors. For one example, in a falling film sulfonation, which is continuous, the mole ratio of $SO_3$ to acyloxy benzene preferably ranges from about 0.9 to 1.1. For one example, in a batch sulfonation, this ratio can range from an initial value of 0 to a maximum value (as at the end of a sulfonation) of about 1.1.

A product of such a sulfonation is presently impossible to analyze directly by conventional techniques because of its reactivity, and so its exact composition in any given instance is presently unknown; however, best available evidence indicates that such product is an adduct of SO₃ and acyloxy benzene.

Digestion

Evidently, during sulfonation, acyloxy benzene forms an adduct with SO₃ at the ester carbonyl group. In the prior art, SO₃ adducts tend to form when aliphatic carboxylic acid esters are sulfonated with SO₃, but such prior art adducts have vastly different characteristics. However, after formation, this present adduct unexpectedly appears to spontaneously rearrange even at low temperatures. Investigation has led to the present discovery that at average temperatures below about 75° C., such rearrangements can be caused to take place in a controlled manner.

The rate of adduct rearrangement is roughly proportional to the temperature. With increasing temperatures over about 75° C., the rate and frequency of side reactions appears to increase while at temperatures below about 15° C., the rate of rearrangement tends to become impractically long for commercial purposes. At temperatures in the high end of the range of about 15° to 75° C., control of the rearranging mass appears to be difficult to maintain, especially in early stages of digestion. In general, the average temperature of digestion is controlled below about 75° C. in order to minimize occurrence of localized overheating. Digestion times longer than about 4 hours or less than about 0.1 hour appear to be impractical commercially, especially when using conventional apparatus, such as a heat exchanger or the like, for the digestion zone.

For example, in the case of phenyl octanoate, the SO₃ adduct requires about 4 hours to digest completely at about 35° C. whereas at about 55° C., digestion is completed in about 15 minutes (about 0.25 hr). The time for substantially complete rearrangement to occur is generally inversely proportional to the temperature of the adduct/sulfonic acid mixture within the ranges taught herein.

It is apparently possible to chill, and then interveningly to store, an SO₃-acyloxy benzene adduct reaction product from sulfonation by using a storage temperature which is typically in the range from about −10° to −20° C. Even such a chilled product will apparently rearrange very slowly with the rate of rearrangement at any given time being influenced by the temperature. However, it is generally presently preferred in the practice of this invention to transfer an adduct effluent from a sulfonation reaction zone directly and immediately into a digestion or stripping zone without intervening storage or holding.

Preferably, during digestion, the acyloxy benzene sulfonic acid being produced is maintained in a liquid form.

By maintaining the digestion temperature within the above-indicated temperature range, the rearrangement of a SO₃-acyloxy benzene adduct takes place with a maximum production of the desired acyloxy benzene sulfonic acid and with a minimum production of other products. Also, with digestion in such a temperature range, color formation, adduct degradation, and by-product formation are minimized.

In a mixture of adduct and acyloxy benzene sulfonic acid formed from adduct, further digestion (and rearrangement) takes place under liquid phase conditions at a temperature below the solidification or melting point temperature of the sulfonic acid. Solidification of such sulfonic acid evidently tends not to occur until the acyloxy benzene sulfonic acid level reaches a critical value which appears to be dependent on structure of the final product in any given case. For example, straight chain acyloxybenzne sulfonic acid levels may reach concentration levels of about 75 to 80% before such an acid solidification occurs.

In one preferred mode of practicing digestion in accord with the present invention, a starting acyloxy benzene is sulfonated as described above under batch conditions in the presence of the low boiling liquid diluent (preferably comprised of SO₂), and digestion is them immediately initiated thereafter. During digestion, the low boiling liquid diluent is evaporated preferably by using reduced pressures.

The rate of evaporation effectively and inherently regulates the digestion temperature. As such diluent evaporates, it cools the rearranging mass. This is particularly effective in regulating in the most critical early stages of digestion when the possibilities for unwanted by-product formation appear to be greatest.

Reduced pressures may be employed if desired to accomplish such evaporation and temperature control. The temperature of the reaction product during such evaporation can conveniently range from about −10° to +15° C.

After such diluent has been effectively completely removed, then the digestion of the reaction mass can be continued at a temperature initially approximating that achieved in the reaction mass at the end of diluent removal, or at a higher temperature, if desired. The temperature employed can be influenced by the equipment being used for digestion. Preferably in this operation, the rearranging reaction product is maintained at a temperature ranging from about 10° to 75° C. for a time sufficient to cause substantially complete rearrangement of the reaction product, thereby to produce a maximum yield of acyloxy benzene sulfonic acid. The total time for digestion (including time for diluent removal and subsequent temperature control) should preferably be within the time periods above indicated.

As indicated, during digestion, in addition to the above-indicated desired rearrangement into acyloxy benzene sulfonic acid, by-products are possible. For example, reaction can take place so as to result in the production of a fatty acid and sulfonated phenol. (Alternatively, for another example, acyloxy benzene can rearrange under conditions of a so-called Fries Rearrangement to cause the ester group to rearrange into a ketone phenol, and such a ketone phenol can further react with a fatty acid by-product to produce various esters.) The number and variety of ultimate rearrangement products which can occur is substantial, and the by-product mixtures achievable are complex in nature. However, carrying out intermediate adduct rearrangements under the digestion conditions herein provided generally maximizes production of acyloxy benzene sulfonic acid and minimizes production of other materials. Thus, examples of by-products produced when controlled digestion is practiced as taught herein may include: unreacted starting acyloxybenzene ester, ketone phenol, ketone ester, sulfones, and the like, but additional and alternative other by-products may be present. The exact quantities of these individual by-products which are present in a given rearranged product of controlled digestion are not now known. These by-products seem generally to be relatively stable materials which do not in themselves appear to affect the stability of the desired sulfonic acid produced.

In general, the intermediate sulfonic acid product produced by the digestion procedures of the present invention is a composition which characteristically comprises on a 100 weight percent total composition basis:

(a) from about 80 to 92 weight percent of acyloxy benzene sulfonic acid, and (b) from about 8 to 20 weight percent of by-products.

The product of the digestion is thus a composition which contains a higher content of acyloxy benzene sulfonic acid than can be obtained by sulfonation alone (without a controlled digestion step) even using the same starting material and identical sulfonation conditions, as the Examples illustrate below. Optimizing of process conditions in any given instance apparently can produce significant differences in such comparative yields, as those skilled in the art will readily appreciate. Such increases in yields are believed to be surprising and unexpected. No other techniques or means for so increasing yields of acyloxy benzene sulfonic acid directly utilizing only $SO_3$ sulfonation and digestion is now known.

The purity of an acyloxybenzene sulfonic acid composition produced by utilizing such digestion can range as above indicated. However, contents of acid above about 93 to 95 weight percent (the exact upper limit not now being known) appear to be not capable of achievement even by the superior process steps of this invention for reasons not now altogether clear, but which are theorized to be associated with the tendency for the intermediate product of the sulfonation step (sometimes termed herein the adduct) to rearrange even under the controlled digestion condition herein employed with only the inherent production of some by-products. By-product production cannot be completely avoided, it is theorized.

In addition to such yield increases, the product of the digestion is a composition which has a lower associated color than can be obtained by sulfonation alone (without a controlled digestion step) even using the same starting material and identical sulfonation conditions, as the Examples illustrate below. As in the case of yields, optimizing of process conditions in any given instance apparently can result in significant color improvements over the prior art as those skilled in the art will readily appreciate. Such improvements in color are believed to be surprising and unexpected. No other technique or means for so increasing color of acyloxybenzene sulfonic acid directly utilizing only $SO_3$ sulfonation and digestion is now known.

The color of a product sulfonic acid largely determines the color of a neutralized and dehydrated final product (see the following description pertaining to these further processing steps). However, for measurement purposes, the color of a neutralized and dehydrated final product is measured. For present purposes, APHA color value (where the sample evaluated is measured as a 10% aqueous solution) is used. For commercial acceptability, the color of a final neutralized and dehydrated product should be below about 150 APHA, and preferably below about 100.

Such low color values cannot be achieved or even approached by using only prior art sulfonation without digestion. For instance, the prior art sulfonation procedure shown in Example 1 below produces a product neutralized acid having an APHA color value in the range from about 250 to 400; yet, when this same procedure is utilized with controlled digestion as shown in Examples 2–4 below, the APHA color value is only about 150. Also, when the procedure of Examples 5 and 6 below is employed, the APHA color value is only about 50 to 60 which value is not more than about 1/5 the value achieved by the prior art sulfonation procedure. Thus, a dramatic improvement in color is provided by the practice of the present invention. Largely because of such color considerations, the combination of batch sulfonation with subsequent digestion as taught herein represents a presently preferred embodiment of this invention.

Neutralization

The desired intermediate product sulfonic acid produced by the foregoing digestion procedures can, if desired, be stored as indicated above, before being further processed. However, in the preferred practice of this invention, such intermediate acid product is promptly (after its formation) admixed with a preformed aqueous solution of a base whose cation selection from the group consisting of alkali metals, alkaline earth metals, and ammonium as indicated above with sodium being presently preferred. Preferably neutralization is accomplished at a temperature below about 15° C. and more preferably below about 5° C. under aqueous liquid phase conditions.

Neutralization in accord with the present invention can be carried out batchwise or continuously. If carried out batchwise, it is preferred preliminarily to dissolve the acyloxybenzene sulfonic acid in water preferably under liquid phase conditions at a temperature as near to 0° C. as practical to minimize hydrolysis of such sulfonic acid ester in water. Preferably, the resulting sulfonic acid aqueous solution contains from about 3 to 30 weight percent on a total solution weight basis of such acid with the balance being water. Thereafter, the aqueous base solution is admixed therewith under liquid phase conditions preferably in approximately an equimolar amount relative to the acyloxy benzene sulfonic acid and preferably at a temperature below about 10° C. Preferably the final pH of the resulting mixture ranges from about 5 to 6.

If neutralization is carried out continuously, it is preferred to bring together continuously the aqueous base solution with such sulfonic acid ester (preferably freshly digested) in a mixing zone or chamber. The mixing takes place rapidly under liquid phase conditions preferably at a temperature ranging from about 0° to 35° C. These continuous mixing conditions minimize hydrolysis of such sulfonic acid ester. The respective quantities of such base solution and such sulfonic acid ester as fed to the mixing zone are continuously regulated so as to maintain the pH of the resulting mixture issuing from the mixing zone in the range from about 4 to 7 and preferably from about 5 to 6.

In general, the product produced by the neutralization procedures above characterized appears to be an aqueous solution or slurry that has an APHA color which is less than about 150 and which comprises on a 100 weight percent total composition basis:

(a) from about 10 to 40 weight percent of an acyloxy benzene sulfonate salt, (b) from about 1.0 to 12.0 weight percent of by-products, and (c) from about 48 to 89 weight percent water.

In such salt, the cation is selected from the group consisting of alkali metals, alkaline earth metals, and ammonium. The acyl group is as defined above. The by-products remain substantially unchanged as now understood.

The by-products present in the salt appear to be substantially identical in type and composition to the by-products above described as being present in a product of controlled digestion produced by the teachings of this invention.

Thus, for example, one presently preferred process of this invention permits production of an acyloxy benzene sulfonate salt which has an APHA color that is less than about 100. Such preferred process comprising the steps of sequentially:

(A) contacting SO$_3$ with at least one acyloxybenzene of the formula:

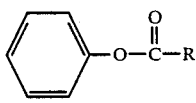

where R is a saturated aliphatic group containing from about 2 to 19 carbon atoms inclusive under liquid phase conditions in the presence of a substantially inert liquid which boils below about 10° C. to produce a reaction product wherein the combined mole ratio of SO$_3$ to acyloxybenzene ranges from about 0.9 to 1.1, (B) evaporating said inert liquid from said reaction product at a rate sufficient to maintain said reaction product at a temperature in the range from about −10° to 15° C., (C) maintaining said resulting reaction product at a temperature in the range from about 10° to 75° C. until said reaction product has been substantially completely rearranged, thereby to produce acyloxybenzene sulfonic acid, and (D) continuously admixing a stream of said acid with a stream of dilute aqueous base solution under liquid phase conditions at a temperature below about 35° C. while maintaining the pH of the resulting mixed solution in the range from about 4 to 7.

Dehydration

The neutralized product, as above characterized and produced by the foregoing neutralization procedures, may either be in an aqueous slurry or aqueous solution form. It may be used as such. It can also be dehydrated or substantially completely dried to produce a solid product (usually and preferably in a particulate form). When dried, the solid product produced is comprised mainly of acyloxy benzene sulfonate salts as the foregoing product compositional description indicates. It is presently preferred to convert such an aqueous neutralized product into a salt in solid, particulate form by drying. For example, a neutralized slurry can be drum dried or spray dried (the latter being presently preferred).

In general, a dried product is a storable solid which comprises on a 100 weight percent total composition basis:

(a) from about 80 to 94 weight percent of an acyloxybenzene sulfonate salt, and (b) from about 6 to 20 weight percent of by-products.

In such salt, the cation is selected from the group consisting of alkali metals, alkaline earth metals, and ammonium. The acyl group is as above defined. The by-products remain substantially unchanged as now understood.

A presently preferred such dried product comprises on a total composition basis from about 85 to 94 weight percent of said acyloxybenzene sulfonate salt, and from about 6 to 15 weight percent of such by-products.

A presently preferred spray drying process comprises spraying such a starting aqueous solution or slurry composition into a drying chamber in the initial form of droplets while simultaneously impinging against said droplets in said chamber an inert gas stream maintained at a temperature ranging from about 100° to 175° C. and thereafter collecting the dried particular composition so resulting.

EMBODIMENTS

The present invention is further illustrated by reference to the following examples. Those skilled in the art will appreciate that other and further embodiments are obvious and within the spirit and scope of this invention from the teachings of these present examples taken with the accompanying specification.

EXAMPLE 1

(Prior Art)

Using a Knaggs/Nussbaum-type falling film sulfonation apparatus as described in the aforementioned Knaggs and Nussbaum U.S. Pat. No. '142, sulfonation of phenyl octanoate (whose composition is shown in Table VII below) carried out under the following conditions:

SO$_3$/Air—5% (vol/vol)
Jacket temperature—8° C.
Irrigation rate—8.4

The term "irrigation rate" has reference to the feed rate in pounds/hr. of the phenyl octanoate per circumferential inch (circumference of tube).

The reaction product from the reactor is collected and the temperature change thereof with respect to time is recorded at measured intervals. The samples are collected and analyzed to determine the percent of octanoyloxy benzene sulfonic acid present in the product composition (on a dry weight basis). The results are shown in Table VIII below:

TABLE VII

| Composition of Phenyl Octanoate (100 Weight Percent Basis) | |
|---|---|
| Phenol | 0.34% |
| Octanoic Acid | 0.44% |
| Phenyl Octanoate | 98.9% |
| Phenyl Decanoate | 0.34% |

TABLE VIII

| Yield of Octanoyloxy Benzene Sulfonic Acid Without Controlled Digestion | | |
|---|---|---|
| Time | Temperature °C. | Active wt. % | Location and Comments |
| 0 sec. | 49 | 34.1 | At reactor outlet |
| 20 sec. | 104 | 75.9 | Stirred in beaker |
| 40 sec. | 98 | 78.5 | Stirred in beaker |
| 60 sec. | — | 77.8 | Stirred in beaker |
| 90 sec. | — | 77.5 | Stirred in beaker |

The percent actives is determined by hyamine-mixed indicator titration.

For reasons of accurate measurement, calculation of yields is here based upon the non-neutralized acid rather than on a neutralized salt prepared therefrom. However, some samples of sulfo phenyl octanoate described in Table VIII are dissolved in ice water and neutralized by addition of 10% aqueous NaOH to pH—5.5. For each sample, the active sodium sulfo phenyl octanoate produced is shown in Table IX.

TABLE IX

| | Salt Yield | |
|---|---|---|
| Time | Temperature °C. | Actives % |
| 0 sec. | 49 | — |
| 20 sec. | 104 | 77.4 |
| 40 sec. | 98 | — |
| 60 sec. | — | 81.4 |
| 90 sec. | — | 80.0 |

It is estimated that these neutralized acid (salt) products have an APHA color of about 275–400 measured as a 10% solids solution in water. This measurement is described in ASTM test procedure number D2108-71.

Thus, in this example, no digestion zone is employed and the effluent from the sulfonation reactor is allowed to experience temperature changes with no effort being made to control exotherm or to cool the reaction product. Hence this procedure is comparable to teachings contained in the aforedescribed Knaggs and Nussbaum U.S. patent.

EXAMPLES 2–4

The sulfonation procedure of Example 1 is repeated with the same phenyl octanoate. Here, however, the effluent from the reactor is immediately charged from the reaction zone into the tube of a shell and tube heat exchanger via an in line continuously operating transfer pump. An in line mixer is positioned in the feed line between the pump and the heat exchanger. Temperature measurements are made at various locations along the transfer lines and along the tube of the heat exchanger. Also, samples are concurrently collected from various locations as follows:
(a) at reactor outlet,
(b) before the pump,
(c) after the pump,
(d) after the mixer, and
(e) after the heat exchanger
Samples are then analyzed to determine the weight percent of acyloxy benzene sulfonic acid recovered. This procedure is repeated three times. The results are recorded in Table X below:

TABLE X

Yield of Octanoyloxy Benzene Sulfonic Acid With Controlled Digestion

| | Time | Temperature °C. | Actives Wt. % | Location |
|---|---|---|---|---|
| Run I (Ex. 2) | 0 sec. | 39 | — | At reactor outlet |
| | 3 sec. | 50 | 36.5 | Before pump |
| | 5 sec. | 70 | 63.4 | After pump |
| | 15 sec. | 71 | 81.3 | Before heat exchanger |
| | 165 sec. | 41 | 82.3 | After heat exchanger |
| Run II (Ex. 3) | 0 sec. | 47 | — | At reactor outlet |
| | 3 sec. | 76 | 51.3 | Before pump |
| | 5 sec. | 80 | 72.4 | After pump |
| | 15 sec. | 72 | 82.8 | Before heat exchanger |
| | 165 sec. | 43 | 82.3 | After heat exchanger |
| Run III | 0 sec. | 44–45 | — | At reactor outlet |

TABLE X-continued

Yield of Octanoyloxy Benzene Sulfonic Acid With Controlled Digestion

| | Time | Temperature °C. | Actives Wt. % | Location |
|---|---|---|---|---|
| (Ex. 4) | 3 sec. | 95 | 58.0 | Before pump |
| | 5 sec. | 90 | 74.7 | After pump |
| | 15 sec. | 79 | 75.3 | Before heat exchanger |
| | 165 sec. | 42 | 83.3 | After heat exchanger |

The results shown in Table X demonstrates that, by the use of the described digestion step, approximately a 5 to 6% increase in yield of octanoyloxy benzene sulfonate is achieved.

Table X also illustrates that when the digestion temperature is allowed to rise above about 75° C., digestion is not permitted to proceed to completion within the 3 to 5 second time frame experienced.

A few of these digested acid products are neutralized at 0° C. and analyzed by the procedure described in Example 1 to obtain information concerning the effect of neutralization on yield. The results are shown in Table XI below:

TABLE XI

| | Salt Yield | |
|---|---|---|
| | Time | Actives % |
| Run I (Ex. 2) | 0 sec. | — |
| | 3 sec. | — |
| | 5 sec. | — |
| | 15 sec. | 85.5 |
| | 165 sec. | 82.8 |
| Run II (Ex. 2) | 0 sec. | — |
| | 3 sec. | — |
| | 5 sec. | — |
| | 15 sec. | 78.4 |
| | 165 sec. | 77.9 |
| Run III (Ex. 3) | 0 sec. | — |
| | 3 sec. | — |
| | 5 sec. | — |
| | 15 sec. | — |
| | 165 sec. | — |

These neutralization results indicate the propriety of using the sulfonic acid as the basis for yield calculation since differences exist between the yield of acid and the yield of salt directly derived therefrom. The exact cause of such differences is unknown, but available evidence indicates that some hydrolysis occurs by this neutralization procedure. Comparison of the yields of salts here produced to the yields of salt produced in Example 1 does not appear to be proper because of the procedural differences involved, especially the temperature of neutralization.

The color of a 10 weight percent solids solution in water of the so neutralized acid is found by APHA analyses to be about 150. This color appears to be properly comparable to the color achieved in the product of Example 1.

EXAMPLE 5

110 grams (0.5 moles) of the same phenyl octanoate is placed in a 500 ml flask fitted with a dry ice-acetone condenser, a stirrer, and a gas inlet tube. Gaseous $SO_2$ is passed into the flask to accomplish batch sulfonation. As the gas passes up the condenser, it liquifies and drops into the flask. Addition is stopped when about 200 mls of liquid $SO_2$ have been added. The reflux temperature ranges from about 0° to −5° C. Good stirring is maintained.

While continuing a slow flow of gaseous SO₂, 41.5 grams (0.52 mole) SO₃ is vaporized in about one hour, under the liquid level, as a co-current stream, to complete sulfonation.

Thereafter, to initiate controlled digestion, the flask is connected to a vacuum source and immersed in a 55° C. water bath and the SO₂ is continuously evaporated over a time of about 45 minutes. During the period of SO₂ evaporation, some digestion under controlled conditions occurs. Digestion temperature is regulated by the temperature of the evaporating SO₂. Foaming is avoided by adjusting the vacuum level. Following removal of SO₂, digestion is continued at 55° C. for fifteen to thirty minutes until rearrangement is completed. The sulfo phenyl octanoate actives thus obtained has the following analysis:

Acidity—3.30 ME/G
Actives—89.0%

Thereafter, the resulting (rearranged) sulfonic acid is slowly added to 1000 mls cold water (0°-5° C.) so that the temperature does not rise above about 10° C. Then, the product resulting is neutralized at 0°-5° C. with added 10% NaOH until the pH reaches about 5.0-6.0. At 0°-5° C. in cold water, the acid is stable for about 4 hours. The neutralized acid is substantially more stable even at room temperatures.

The resulting solution can be either spray dried or drum dried to produce a white powder. For example, spray drying in a laboratory sized BUCHI 190 mini spray dryer is accomplished under the following conditions:

Slurry concentration: 15% solids
Slurry flow rate: 3-4 cc/min.
Air flow: 45 M³/min.
Air temperature in: 130° C.
Air temperature out: 90° C.

This spray dried product is a white powder having neutralized acid (salt) actives of 89.1%.

The color of a 10 weight percent solids solution in water is found by APHA analysis to be 50. This color appears to be properly comparable to the color achieved in the products of Example 1 and of Examples 2-4.

EXAMPLE 6

Following the procedure of Example 5, 117 grams (0.5 mole) of phenyl pelargonate (whose composition is shown in Table XII below) is treated with 41.8 grams (0.52 mole) SO₃). The resulting degassed and digested sulfo phenyl pelargonate had the following analysis:

Acidity—3.16 ME/G.
Actives—89%
Neutralization and spray drying as in Example 5 produced a white powder with 90.7% actives. The APHA color is 60 (10% solids).

TABLE XII

| Composition of Phenyl Nonanonate (100 weight percent basis) | |
|---|---|
| phenol | 0.37% |
| 2-methyl phenyl octanoate | 2.59% |
| phenyl nonanonate | 96.57% |

Similar results to those achieved in the procedures of Examples 2-4 and Examples 5 and 6 are found to occur when:

(A) the acyloxy benzene starting material has an acyl group which contains 10 or 12 carbon atoms, (B) the acyloxy benzene starting material is a mixture of different acyloxy benzene compounds wherein the acyl group is comprised of 8, 9, 10, 11, and 12 carbon saturated aliphatic chains.

Lower yields when such a mixed acyloxybenzene starting material is employed are not observed compared to yields obtained with such single acyloxybenzene starting materials. Also, changes in process conditions when such a mixed acyloxybenzene starting material is employed are not needed over those employed for such pure starting materials in order to obtain such comparable yields.

As the molecular weight of a starting acyloxybenzene increases, a slightly higher digestion temperature is presently preferred compared to the digestion temperature employed for a lower molecular weight such starting material.

As is apparent from the foregoing specification, the invention is susceptible of being embodied with various alterations and modifications which may differ particularly from those that have been described in the preceding specification and description. For this reason, it is to be fully understood that all of the foregoing is intended to be merely illustrative and is not to be construed or interpreted as being restrictive or otherwise limiting of the present invention, excepting as it is set forth and defined in the hereto-appended claims.

I claim:

1. A process for making an acyloxy benzene sulfonate salt of at least about 80 weight percent purity on a total composition dry weight basis from a corresponding acyloxy benzene comprising the steps of
   (a) contacting substantially pure acyloxy benzene with SO₃ at a temperature ranging from about −20° to 50° C. to produce an intermediate reaction product which comprises about a 1:1 molar adduct of said SO₃ and said acyloxy benzene,
   (b) maintaining said intermediate reaction product at an average temperature in the range from about 25° to 75° C. for a time inversely ranging from about 0.1 to 4 hours sufficient to produce a product composition containing at least about 80 weight percent of the corresponding acyloxy benzene sulfonic acid, and
   (c) admixing the resulting said acyloxy benzene sulfonic acid with an aqueous solution of a base of a cation selected from the group consisting of alkali metal salts, alkaline earth metals, and ammonium to produce an aqueous solution containing the corresponding salt of said acyloxy benzene sulfonic acid.

2. The process of claim 1 wherein said acyloxy benzene is cahractersized by the formula:

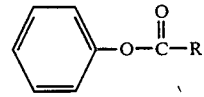

where R is a saturated aliphatic group containing from 2 through 19 carbon atoms.

3. The process of claim 2 wherein said sulfonation is carried out in a zone wherein the average temperature ranges from about −30° to +50° C., and the mole ratio of said SO₃ to said acyloxy benzene ranges from about 0.9:1 to 1.1:1.

4. The process of claim 2 wherein each said aliphatic group is an alkyl group which contains from 7 through 11 carbon atoms.

5. The process of claim 2 wherein said contacting is carried out in a liquid phase in the presence of a diluent.

6. The process of claim 5 wherein said contacting is carried out with said acyloxybenzene being in a liquid state.

7. The process of claim 1 wherein said digesting is carried out at an average temperature ranging from about 40° to 75° C.

8. The process of claim 1 wherein said admixing is carried out continuously and the product neutralized solution has a pH in the range from about 4.5 to 7.

9. The process of claim 1 wherein the final product solution has a pH ranging from about 3 to 8 and wherein the concentration of said salt of said acyloxy benzene sulfonic acid ranges from about 5 to 60 weight percent based on total aqueous solution weight.

10. A process for making an acyloxy benzene sulfonate salt which has an APHA color that is less that about 100 comprising the steps of sequentially:
(A) contacting $SO_3$ with at least one acyloxybenzene of the formula:

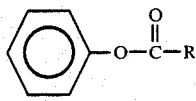

where R is a saturated aliphatic group containing from about 2 to 19 carbon atoms inclusive under liquid phase conditions in the presence of a substantially inert liquid to produce a reaction product wherein the combined mole ratio of $SO_3$ to acyloxybenzene ranges from about 0.9 to 1.1,
(B) evaporating said inert liquid from said reaction product at a rate sufficient to maintain said reaction product at a temperature from about −10° to 15° C.
(C) maintaining said resulting reaction product at a temperature in the range from about 10° to 75° C. for a time inversely ranging from about 0.1 to about 4 hours until said reaction product has been substantially completely rearranged, thereby to produce acyloxybenzene sulfonic acid, and
(D) admixing said acid with dilute aqueous base solution under liquid phase conditions at a temperature below about 35° C.

11. The process of claim 10 wherein said acyloxybenzene sulfonic acid is dissolved in water under liquid phase conditions at a temperature below about 5° C. to produce a dilute aqueous acid solution and said solution is then so admixed with said base solution.

12. The process of claim 10 wherein said resulting mixed slurry is spray dried.

13. In a sulfonation process for making a sulfonated salt by sulfonating with $SO_3$ and neutralizing, the improvement which comprises reacting an acyloxy benzene with $SO_3$ at low temperatures followed by a controlled rearrangement step between said sulfonating and said neutrualizing, said controlled rearrangement step comprising maintaining the sulfonation reaction product at a temperature of from about 15° to 75° C. until said reaction product is substantially completely rearranged.

* * * * *